United States Patent
Carro Aramburu et al.

(10) Patent No.: US 12,351,833 B2
(45) Date of Patent: Jul. 8, 2025

(54) UNSPECIFIC PEROXYGENASE ENZYME VARIANTS FOR SELECTIVE FATTY ACID EPOXIDATION OR HYDROXYLATION

(71) Applicant: CONSEJO SUPERIOR DE INVESTIGACIONES CIENTÍFICAS (CSIC), Madrid (ES)

(72) Inventors: Juan Carro Aramburu, Madrid (ES); Alejandro González Benjumea, Seville (ES); Carmen Aranda Oliden, Seville (ES); Ana Gutiérrez Suárez, Seville (ES); Angel T. Martínez Ferrer, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 588 days.

(21) Appl. No.: 17/616,489

(22) PCT Filed: Jun. 3, 2020

(86) PCT No.: PCT/EP2020/065294
§ 371 (c)(1),
(2) Date: Dec. 3, 2021

(87) PCT Pub. No.: WO2020/245159
PCT Pub. Date: Dec. 10, 2020

(65) Prior Publication Data
US 2022/0228132 A1 Jul. 21, 2022

(30) Foreign Application Priority Data
Jun. 7, 2019 (EP) ..................... 19382479

(51) Int. Cl.
C12N 9/08 (2006.01)
C12N 1/20 (2006.01)
C12N 15/62 (2006.01)
C12N 15/70 (2006.01)
C12P 17/02 (2006.01)

(52) U.S. Cl.
CPC ............ *C12N 9/0065* (2013.01); *C12N 1/20* (2013.01); *C12N 15/625* (2013.01); *C12N 15/70* (2013.01); *C12P 17/02* (2013.01); *C12Y 111/02001* (2013.01); *C07K 2319/02* (2013.01); *C12N 2800/101* (2013.01)

(58) Field of Classification Search
None
See application file for complete search history.

(56) References Cited

U.S. PATENT DOCUMENTS 9,534,208 B2 * 1/2017 Landvik ............. C11D 3/38636
10,465,173 B2 * 11/2019 Landvik .................. C12P 13/02

FOREIGN PATENT DOCUMENTS

EP       3392341 A1    10/2018
WO    2016207373 A1    12/2016

OTHER PUBLICATIONS

Chahinez Aouf, "The Use of Lipases as Biocatalysts for the Epoxidation of Fatty Acids and Phenolic Compounds", Journal, 2014, 1740-1754, vol. 16, Green Chemistry.
Alejandro Sustaita-Rodriguez, "Lipase Catalyzed Epoxidation of Fatty Acid Methyl Esters Derived from Unsaturated Vegetable Oils in Absense of Carboxylic Acid", Journal, 2012, 1-7, vol. 12, Chemistry Central Journal.
Fabian Haitz, "Chemo-Enzymatic Epoxidation of Lallemantia Iberica Seed Oil: Process Development and Economic-Ecological Evaluation", Article, 2017, 1-21, Applied Biochemical Biotechnology.
Richard T. Ruettinger, "Epoxidation of Unsaturated Fatty Acids by a Soluable Cytochrome P-450-dependent System from Bacillus Megaterium", Journal, 1981, 5728-5734, vol. 256, No. 11, The Journal of Biological Chemistry.
Angela Kockritz, "Synthesis of Azelaic Acid from Vegetable Oil-Based Feedstocks", Journal, 2011, 83-91, vol. 113, European Journal of Lipid Science and Technology.
Li Han, "Designing and Creating a Synthetic Omega Oxidation Pathway in *Saccharomyces cerevisiae* Enables Production of Medium-Chain a, w-Dicarboxylic Acids", Article, 2017, 1-12, vol. 8, Frontiers in Microbiology.
Sun-Ki Kim, "Biosynthesis of w-hydroxy fatty acids and related chemical from natural fatty acids by recombinant *Escherichia coli*", Article, 2018, 1-9, Applied Microbiology and Biotechnology.
Carmen Aranda, "Selective Epoxidation of Fatty Acids and Fatty Acid Methyl Esters by Fungal Peroxygenases", Article, 2018, 1-5, vol. 10, No. 18, ChemCatChem—The European Society Journal for Catalysis.
Patricia Molina-Espeja, "Directed Evolution of Unspecific Peroxygenase from Agrocybe Aegerita", Journal, 2014, 3496-3507, vol. 80, No. 11, Applied and Environmental Microbiology.
Patricia Molina-Espeja, "Tandem-Yeast Expression System for Engineering and Producing Unspecified Peroxygenase", Journal, 2015, 29-33, vol. 73-74, Enzyme and Microbial Technology.
Glenn Grobe, "High-Yield Production of Aromatic Peroxygenase by the Agaric Fungus Marasmius Rotula", Journal, 2011, 1-1, vol. 1, No. 31, AMB Express.

* cited by examiner

*Primary Examiner* — Blaine Lankford
(74) *Attorney, Agent, or Firm* — Hayes Soloway P.C.

(57) ABSTRACT

The invention relates to a recombinant *Marasmius rotula* unspecific peroxygenase (rMroURO) and two mutants thereof, wherein said mutants show enhanced selectivity towards either the epoxidation or the (sub)terminal ω/(ω-1)-hydroxylation of unsaturated fatty acids. The invention also refers to the use of these enzyme variants for the specific epoxidation or hydroxylation of fatty acids such as oleic acid, linoleic acid and/or alpha-linolenic acid.

4 Claims, 9 Drawing Sheets

Specification includes a Sequence Listing.

UNSPECIFIC PEROXYGENASE ENZYME VARIANTS FOR SELECTIVE FATTY ACID EPOXIDATION OR HYDROXYLATION

CROSS-REFERENCE TO RELATED APPLICATIONS AND PRIORITY

This patent application claims priority from PCT Application No. PCT/EP2020/065294 filed Jun. 3, 2020, which claims priority from EP patent application Ser. No. 19/382,479.4 filed Jun. 7, 2019. Each of these patent applications are herein incorporated by reference in its/their entirety.

The invention belongs to the field of chemical processes catalysed by engineered enzymes, specifically to recombinant and mutated fungal, preferably from *Marasmius rotula*, unspecific peroxygenases (MroUPOs). In particular, the invention relates to a recombinant MroUPO (rMroUPO) and mutants thereof whose selectivity towards either epoxidation or hydroxylation of unsaturated fatty acids is improved.

BACKGROUND ART

Oxyfunctionalisation reactions—that is, the introduction of oxygen atoms into different molecules—are key in chemistry since they are interesting for a number of industrial processes. Moreover, vegetable oils are important raw materials to produce a plethora of different products due to their renewable nature and widespread availability. Those are tri-esters of glycerol with fatty acids, among which the unsaturated ones are abundant in these oils.

On the one hand, epoxidation of the double bonds (i.e. unsaturations) of fatty acids is one of the most common oxyfunctionalisation reactions catalysed in oil-based industry. Epoxidation of unsaturated fatty acids—a main constituent of soybean, linseed and other plant oils—has high interest for the industrial production of a variety of chemicals and intermediates, including adhesive and binder components among others. Thus, epoxides derived from fatty acids are used as stabilizers, plasticizers and as cross-linking agents in the preparation of adhesives and binders. Generally, epoxides arise from the reaction of the fatty-acid double bonds with peracids. The most known method to industrially produce epoxides relies on the Prileschajew reaction. Such reactions act through percarboxylic acids generated using strong mineral acids ($HNO_3$, $H_2SO_4$). There exist also other chemical methods that use ion-exchange resins and different catalysts as salts and metals. Nevertheless, enzymatic processes to epoxidize unsaturated oils have been developed (Aouf, C., et al., 2014, Green Chem., 16:1740-1754; Sustaita-Rodriguez, A., et al., 2018, Chemistry Central Journal, 12:39; Haitz, F., et al., 2018, Applied Biochemistry and Biotechnology, 185:13-33), but the latter rely on the same percarboxylic acids required in the chemical processes, although lipases are used to catalyse its formation. This chemo-enzymatic approach therefore maintains the drawbacks related to peracid-based epoxidation. On the contrary, exclusively enzymatic epoxidation of fatty acids has been achieved by the enzymes P450s (Ruettinger, R. T. and Fulco, A. J., 1981, J. Biol. Chem. 256:5728-5734). Nevertheless, problems associated with their low stability and frequent requirement for auxiliary substrates or enzymes prevent industrial implementation, in spite of numerous studies on their reaction mechanisms.

On the other hand, the hydroxylation of fatty acids may give rise to a variety of compounds depending on the number of hydroxylations and the positions that are oxygenated. Especially, subsequent hydroxylations at the last carbon atom (the so-called w-carbon), give rise to di-carboxylic acids, which are interesting as monomers for the polymer industry (nylons, polyesters, polyamides) and fragrances. Chemical synthesis of w-hydroxylated fatty acids, which are precursors of di-carboxylic acids, is difficult because of the reaction conditions required: high temperatures and pressures, strong mineral acids and oxidants and environmentally harmful reactants (Köckritz, A. and Martin, A., 2011, Eur. J. Lipid Sci. Technol., 113:83-91). Several successful attempts have been made to produce both ω-hydroxylated fatty acids and their derivatives, α,ω-di-carboxylic acids by biocatalytic means. Both whole-cell systems as well as isolated enzymatic cascades employing either P450s (Han, L., et al., 2017, Frontiers in Microbiology, 8:2184) or alcohol dehydrogenases and/or Baeyer-Villiger monooxygenases (Kim, S. K. and Park, Y. C., 2019, Applied Microbiology and Biotechnology, 103:191-199) to oxygenate the fatty acids at the w-position have been described.

In this sense, the so-called unspecific peroxygenases (UPOs, EC 1.11.2.1), fungal secreted enzymes that are phylogenetically and biochemically unrelated to P450s, although they share a range of substrates and enzymatic activities, are promising biocatalysts. UPOs present the advantage that they directly use $H_2O_2$ as O donor and electron acceptor, and thus, they do not require auxiliary flavin-containing enzymes (or protein modules) nor NADPH sources, as P450s usually do. Among the UPOs available, the one from the fungus *Marasmius rotula* (MroUPO) is able to epoxidize and oxygenate fatty acids and fatty acid methyl esters. However, this enzyme exhibits promiscuous activities that yield a mixture of epoxides and epoxidized derivatives (hydroxylated, di-carboxylic and keto derivatives) when reacting with unsaturated fatty acids (Aranda, C., et al., 2018, ChemCatChem, 10:3964-3968).

Therefore, improved *Marasmius rotula* UPOs with enhanced selectivity towards either epoxidation or ω-hydroxylation of unsaturated fatty acids are needed in the industrial chemistry field, particularly in oxyfunctionalization reactions of industrial interest.

Furthermore, despite the fact that UPOs are widespread in fungi (and some fungus-like organisms) with over 2000 upo-type genes identified in sequenced genomes and databases, which constitutes a huge repertoire of potential biocatalysts with different oxygen transfer capabilities, until now only two upo genes from genomes/databases (corresponding to the basidiomycete *Coprinopsis cinerea* and the ascomycete *Humicola insolens*) have been heterologously expressed (by Novozymes A/S in *Aspergillus oryzae* host) and the resultant recombinant enzymes (rCciUPO and rHinUPO) evaluated for oxygenation reactions. Heterologous expression is required not only to explore the variety of UPOs in genomes, but also to understand the reaction mechanisms of these enzymes and to tailor their catalytic and operational properties for industrial biocatalysis.

Apart from the work of Novozymes mentioned above, additional expression of wild-type upo genes as recombinant proteins has not been reported to date. A way to partially solve this limitation came out from the application of enzyme directed molecular evolution to obtain mutated variants (rAaeUPO) tailored for expression in *Saccharomyces cerevisiae* (Molina-Espeja, P., et al., 2014, Appl. Environ. Microbiol., 80, 3496-3507), which were later transferred to *Pichia pastoris* (Molina-Espeja, P., et al., 2015, Enzyme Microb. Technol., 73-74, 29-33). However, the evolved rAaeUPO obtained structurally differs from the wild-type enzyme, as shown by comparison of their crystal structures.

Therefore, in view of the above drawbacks, there is also a need in the field regarding the heterologous expression of soluble and active UPOs.

DESCRIPTION OF THE INVENTION

The invention presented herein solves the problems mentioned above by providing a recombinant unspecific peroxygenase (UPO) enzyme (rMroUPO) that comprises the amino acid sequence shown in SEQ ID NO: 1 and that is encoded by an optimized polynucleotide sequence of the *Marasmius rotula* UPO (MroUPO) gene (SEQ ID NO: 9), which may be thus heterologous expressed in a host cell as an active enzyme, and also mutants thereof whose selectivity towards either epoxidation or hydroxylation of unsaturated fatty acids is improved.

The present invention provides, in particular, a recombinant *Marasmius rotula* unspecific peroxygenase (rMroUPO) and two mutants thereof, wherein said mutants show enhanced selectivity towards either the epoxidation of fatty-acid unsaturations or the (sub)terminal ω- or (ω-1)-hydroxylation of the said unsaturated fatty acids. These mutants have been generated by means of rational design of the mentioned rMroUPO through site-directed mutagenesis.

*Marasmius rotula* unspecific peroxygenase (MroUPO) is capable of introducing oxygen atoms into the fatty acid molecules in the form of hydroxyl groups at various carbons of the molecule, or epoxides between the two carbons bearing the unsaturations. Therefore, the reaction of the said unspecific peroxygenase with unsaturated fatty acids results in a mixture of hydroxylated and epoxidized products. On the one hand, the I153T mutated variant of the present invention, created by rational design, shows improved selectivity towards the epoxidation of several unsaturated fatty acids compared to the MroUPO. On the other, the I153F/S156F mutated variant of the invention was also designed so that its activity is restricted to hydroxylation of the terminal and sub-terminal carbons and thus gives rise to hydroxy-, keto- and di-acid products. Unlike what has been published regarding the balance between epoxidation and hydroxylation catalysed by P450s—in which the redox state of the O atom bound to the heme of the activated enzyme controls its reactivity—, the above mentioned UPO variants rely on steric effects to tune the said balance. In this way, the I153T variant slightly increases the width of the heme channel, thus allowing the fatty acids unsaturations to approach closer to the O bound to heme, promoting epoxidation. In contrast, the I153F/S156F variant displays a narrower heme access channel than the MroUPO enzyme that prevents the fatty acids from entering the active site in the configuration required for epoxidation. In this latter case only the terminal and sub-terminal positions (ω and ω-1) are able to approach the cofactor of the enzyme, which causes its inability to epoxidize and fosters the hydroxylation at the mentioned positions.

Therefore, in the present invention, the inventors demonstrate that:
The rMroUPO enzyme may be successfully expressed as a soluble, active enzyme in a heterologous system thanks to the optimization of its encoding polynucleotide sequence designed herein,
Its I153T mutated variant increases the selectivity towards epoxidation of unsaturated fatty acids compared to the rMroUPO. This is illustrated in the examples below by the reactions of rMroUPO I153T mutated variant with three unsaturated fatty acids—oleic, linoleic and α-linolenic acids—, with which the said variant augments by 4-, 2.7- and 14.6-fold, respectively, the epoxidation selectivity of rMroUPO, and
Its I153F/S156F mutated variant completely abolishes the epoxidation activity and only shows hydroxylation of unsaturated fatty acids, as exemplified below by its reaction with oleic acid.

In summary, in this invention, a MroUPO gene has been optimized and heterologously expressed obtaining a recombinant MroUPO (rMroUPO) as an active soluble enzyme. Then, guided by the crystal-structure of the active site, this rMroUPO has been engineered to tune its epoxidizing vs hydroxylating activities on mono- and poly-unsaturated (18-carbon) fatty acids.

Thus, one aspect of the invention refers to an optimized polynucleotide sequence with at least 90%, 91%, 92%, 93%, 94%, 95%, 96%, 97%, 98% or 99% sequence identity with SEQ ID NO: 9, preferably comprising, more preferably consisting of, the SEQ ID NO: 9, that encodes an unspecific peroxygenase enzyme that comprises, preferably consists of, the amino acid sequence shown in SEQ ID NO: 1.

Another aspect of the invention refers to an unspecific peroxygenase enzyme (UPO) variant that comprises an amino acid sequence at least 90%, 91%, 92%, 93%, 94%, 95%, 96%, 97%, 98% or 99% identical to SEQ ID NO: 1, preferably which comprises the SEQ ID NO: 1, more preferably which consists of the SEQ ID NO: 1, and further comprises the amino acid substitution I153T.

Another aspect of the invention refers to an unspecific peroxygenase enzyme (UPO) variant that comprises an amino acid sequence at least 90%, 91%, 92%, 93%, 94%, 95%, 96%, 97%, 98% or 99% identical to SEQ ID NO: 1, preferably which comprises the SEQ ID NO: 1, more preferably which consists of the SEQ ID NO: 1, and further comprises the amino acid substitutions I153F and S156F.

Another aspect of the invention refers to a recombinant peroxygenase enzyme, hereinafter "the recombinant enzyme of the invention" or "the enzyme of the invention", that comprises the amino acid sequence shown in SEQ ID NO: 1, wherein said enzyme is encoded by a polynucleotide sequence with at least 90%, 91%, 92%, 93%, 94%, 95%, 96%, 97%, 98% or 99% sequence identity with SEQ ID NO: 9, preferably by the polynucleotide sequence shown in SEQ ID NO: 9. This enzyme is a recombinant *Marasmius rotula* unspecific peroxygenase enzyme, and it is also called herein "rMroUPO".

SEQ ID NO: 9 of the present invention is, therefore, a polynucleotide sequence which has been optimized, from the wild type MroUPO gene, in order to be heterologously expressed in a host cell, preferably in a prokaryotic host cell, more preferably in an *E. coli* cell, giving rise to a soluble and active recombinant MroUPO (rMroUPO).

In a preferred embodiment, the rMroUPO referred to in the present invention consists of the amino acid sequence shown in SEQ ID NO: 1.

"Unspecific peroxygenases" (UPOs, EC 1.11.2.1) are heme-thiolate enzymes secreted by fungi and characterized by promiscuous oxygen transfer activities, which make them "dream catalysts" for difficult oxyfunctionalization reactions of industrial interest. The cysteine ligand of UPO heme iron and the enzyme reaction chemistry are reminiscent of P450s. Nevertheless, their protein sequences show that they are fully unrelated to P450s from both phylogenetic and biochemical points of view. Concerning the latter, their extracellular nature—opposed to the intracellular nature of P450s—and consequent higher stability, together with their self-sufficient monooxygenase activity (only requiring $H_2O_2$ to be activated, in contrast to P450s, which normally require a flavin-containing auxiliary enzyme or protein module and a source of reducing power), confer biotechnological advantages to UPOs.

The term "recombinant", in this invention, means that the enzyme has been artificially produced (and purified) through its heterologous expression in an adequate transformed host cell. "Heterologous expression" is the protein expression carried out in a host cell different from the cell which is the natural source of said protein, in the context of the present invention different from *Marasmius rotula*.

In another preferred embodiment, the enzyme of the invention comprises the amino acid substitution I153T. This enzyme will be also called in the present invention "the first variant of the invention". More preferably, this first variant of the invention which comprises or consists of the SEQ ID NO: 1 and comprises the amino acid substitution I153T is the enzyme variant shown in the SEQ ID NO: 2.

In another preferred embodiment, the enzyme of the invention comprises the amino acid substitutions I153F and S156F. This enzyme will be also called in the present invention "the second variant of the invention". More preferably, this second variant of the invention which comprises or consists of the SEQ ID NO: 1 and comprises the amino acid substitutions I153F and S156F is the enzyme variant shown in the SEQ ID NO: 3.

Positions 153 and 156 referred to in the present invention relate to positions in the entire sequence shown in SEQ ID NO: 1.

Single amino acids in an amino acid sequence are represented herein as XN, where X is the amino acid in the sequence (designated by means of the one letter code universally accepted in amino acid nomenclature) and N is the position in the sequence. Amino acid substitutions are represented herein as $X_1NX_2$, where $X_1$ is the amino acid in the sequence shown in the SEQ ID NO: 1, $X_2$ is the new amino acid in the sequence of the mutated enzyme (variant) and N is the position in the amino acid sequence in relation to the positions of the sequence shown in SEQ ID NO: 1.

Amino acid substitutions described herein can be obtained using genetic engineering techniques or recombinant DNA, such as for example by mutating the encoding sequence of the SEQ ID NO: 1 (i.e. SEQ ID NO: 9) by means of directed mutagenesis or they can be obtained by means of chemical synthesis of the nucleotide sequences which code for the variants of the invention that carry the amino acid substitutions.

The terms "variant" or "mutant", as used herein, relate to a *Marasmius rotula* unspecific peroxygenase enzyme (MroUPO) which derives from the recombinant enzyme of the invention (rMroUPO) but whose amino acid sequence has been artificially modified (mutated), preferably by means of one or more substitutions of one or more amino acids, in order to show optimized properties. Therefore, the variants of this invention have different amino acid sequences to that of the rMroUPO enzyme of this invention. In the context of the present invention, "optimized properties" are, preferably, an improved selectivity for epoxidation or hydroxylation of unsaturated fatty acids.

The variants of the invention may be produced by chemical synthesis or recombinantly by an organism or host cell that expresses a nucleotide sequence that encodes the variant of the invention described herein. Said nucleotide sequence is obtained by means of human intervention, by modifying the nucleotide sequence that encodes the rMroUPO. The term "modification" means any chemical modification of the amino acid or nucleic acid sequence of the rMroUPO sequence.

Therefore, the variants of the invention can be synthesised, for instance, but without limitations, in vitro. For example, by means of the synthesis of solid-phase polypeptides or recombinant DNA approaches. Variants of the invention can be produced in a recombinant manner, including their production as mature polypeptides or as pre-proteins that include a signal peptide.

The recombinant enzyme of the invention (rMroUPO, which comprises or consists of SEQ ID NO: 1) or the variants of the invention (which comprises or consists of SEQ ID NO: 2 or SEQ ID NO: 3) may further comprise a signal peptide in its N-terminal end, preferably the signal peptide shown in SEQ ID NO: 4.

Another aspect of the invention refers to a polynucleotide sequence that encodes the enzyme of the invention or the variants of the invention, hereinafter "the polynucleotide of the invention".

Due to the degeneration of the genetic code, various nucleotide sequences can encode the same amino acid sequence. In accordance with the present invention, an isolated "nucleic acid molecule", "nucleotide sequence", "nucleic acid sequence" or "polynucleotide" is a nucleic acid molecule (polynucleotide) that has been eliminated from its natural medium (i.e. it has been subjected to human manipulation) and can include DNA, RNA or DNA or RNA derivatives, including cDNA. The nucleotide sequence of the present invention may or may not be chemically or biochemically modified and can be artificially obtained by means of cloning and selection methods or by means of sequencing.

The polynucleotide sequence of the invention can encode the mature enzyme or a pre-protein that must be subsequently processed and that consists of a signal peptide, preferably the signal peptide shown in the SEQ ID NO: 4, linked to the mature enzyme.

The polynucleotide sequence of the present invention may also comprise other elements, such as introns, non-encoding sequences at ends 3' and/or 5', ribosome binding sites, etc. This nucleotide sequence can also include encoding sequences for additional amino acids that are useful for the purification or stability of the encoded enzyme.

The polynucleotide sequence of the invention can be included in a genetic construct, preferably in a recombinant expression vector. Said genetic construct may further comprise one or more sequences for regulating the gene expression, such as promoters, terminators, enhancers, etc.

Thus, another aspect of the invention refers to a genetic construct, hereinafter "the genetic construct of the invention", that comprises the polynucleotide of the invention. In a preferred embodiment, the genetic construct of the invention is an expression vector, more preferably a plasmid.

The genetic construct of the invention will generally be constructed such that the polynucleotide of the invention is positioned adjacent to and under the control of (i. e., operably linked to) an effective promoter. In certain cases, the promoter will be a prokaryotic promoter where the genetic construct is adapted for expression in a prokaryotic host cell. In other cases, the promoter will be a eukaryotic promoter where the genetic construct is adapted for expression in a eukaryotic host cell. In the latter cases, the genetic construct will typically further include a polyadenylation signal at position 3' of the carboxy-terminal end, and within a transcriptional unit of the encoded polypeptide. Promoters of particular utility in the genetic construct of the invention are mammalian promoters, cytomegalovirus promoters, baculovirus promoters or bacterial promoters, depending upon the host cell used for the recombinant expression of the enzyme or variant of the invention. Preferred promoters are bacterial promoters. Examples of prokaryotic promoters useful for the present invention include, but not limited to, *E. coli* trp, recA, lacZ, lacI, tet, gal, trc, or tac gene promoters, or the *B. subtilis* α-amylase gene promoter.

The expression "gene construct", "genetic construct" or "nucleic acid construct", as used herein, relates to a functional unit required to transfer or express a nucleic acid sequence of interest, herein the polynucleotide sequence of the invention as described, and regulatory sequences including, for example, a promoter, operably linked to the sequence that encodes the enzyme or variant of the invention, in an expression system. It refers to a nucleic acid molecule, mono or bicatenary, which is isolated from a natural gene or that is modified to contain nucleic acid segments in such a manner that they would otherwise not exist in nature. The expression "nucleic acid construct" is synonymous to the expression "expression cassette" when the construct of nucleic acid contains the control sequences required for the expression of the encoding sequence.

The term "expression vector", also known as "expression construct", relates to a DNA molecule, linear or circular, that comprises the polynucleotide sequence of the invention operably linked to additional segments that assist the transcription of the encoded enzyme. Generally, a plasmid is used to introduce a specific nucleic acid sequence of interest in a target cell. Once the expression vector is in the interior of the cell, the enzyme encoded by the nucleic acid sequence is produced by means of the ribosome complexes of the cellular transcription and translation machinery. The expression vector is often subject to engineering to contain regulatory sequences that act as enhancer and promoter regions leading to an efficient transcription of the nucleic acid sequence carried on the expression vector. The objective of a well-designed expression vector is the production of large amounts of stable mRNA and, therefore, proteins. The expression vector of the invention is introduced in a host cell such that the vector remains as a chromosome constituent or as an extra-chromosome self-replicating vector.

The term "expression" relates to the process whereby the enzyme of the invention and variants thereof are synthesised from a polynucleotide. The term includes the transcription of the polynucleotide in a messenger RNA (mRNA) and the translation of said mRNA into a protein or polypeptide. The term also includes the secretion of the protein or polypeptide as a soluble and active enzyme.

Examples of useful expression vectors are plasmids, phages, cosmids, phagemids, autonomously replicating sequence (ARS), yeast artificial chromosomes (YAC), bacterial artificial chromosomes (BAC), human artificial chromosomes (HAC) or viral vectors, such as adenovirus, baculovirus, retrovirus, lentivirus, adeno-associated viral vector (AAV) or any other type of DNA molecule capable of replicating in the interior of a prokaryotic or eukaryotic cell, preferably prokaryotic cell. In a preferred embodiment, the plasmid to which this invention refers is a pET23b plasmid.

The variants of the invention can be prepared using any means known in the state of the art, such as the modification of the DNA sequence that encodes the rMroUPO of the invention (SEQ ID NO: 9), transformation of the modified DNA sequence in an adequate host cell and expression of the modified DNA sequence to obtain the variant.

Thus, another aspect of the invention refers to a host cell, hereinafter "the host cell of the invention", that comprises the polynucleotide sequence of the invention or the genetic construct of the invention.

The host cell of the invention may be either a eukaryotic or a prokaryotic host cell, preferably a prokaryotic host cell. A host cell is the recipient of an expression vector, cloning vector or any other DNA molecule. Therefore, it includes any cultivable cell that may be modified through the introduction of DNA not naturally contained therein. A suitable host cell is that in which the polynucleotide of the invention may be expressed, giving rise to a stable and active enzyme of the invention or variant of the invention. The selection of an appropriate host cell may also be influenced by the election of the detection signal used.

In a more preferred embodiment, the host cell of the invention is an *Escherichia coli* cell, even more preferably an *E. coli* BL21 C41 cell or an *E. coli* DH55a cell.

Another aspect of the invention refers to the use of the host cell of the invention for producing the enzyme of the invention or the variants of the invention.

The host cell according to the invention may be cultivated for such purpose. A host cell culture relates to the in vitro process of maintaining and growing host cells. Cell cultures need controlled conditions of temperature, pH, percentages of gases (oxygen and carbon dioxide), in addition to the presence of the adequate nutrients to allow cellular viability and division. The skill in the art will know which conditions must be applied to the cell culture depending on the requirements of the selected host cell. Cell cultures can be carried out in solid substrates, such as agar, or in a liquid medium, which enables the expansion of large amounts of cells in suspension. Once the cell of the invention has been cultivated and the enzyme of the invention or the variant of the invention has been expressed, it can be purified. The term "to purify", as used in the description, relates to the isolation of the enzyme of the invention or the variant of the invention from the other polypeptides present in the culture medium in which the host cell of the invention has grown. The isolation or purification can be carried out using differential solubility techniques, chromatography, electrophoresis or isoelectric focusing. Chromatography techniques can be based on molecular weight, ion charge (based on the ionisation state of the amino acids under working conditions), the affinity of the protein for certain matrices or chromatographic columns, or by means of purification tags, and can be carried out on a column, on paper or on a plate. The isolation can be carried out, for example, by means of precipitation with ammonium sulphate, fast protein liquid chromatography (FPLC) or high-performance liquid chromatography (HPLC), using automated systems that significantly reduce purification time and increase purification efficiency.

Another aspect of the invention refers to the use of the recombinant enzyme of the invention for the epoxidation and hydroxylation (both) of unsaturated fatty acids. This use refers to the recombinant enzyme of the invention comprising or consisting of the SEQ ID NO: 1.

The term "unsaturated fatty acids", as used in the present invention, includes both mono- and poly-unsaturated fatty acids.

As previously mentioned, and as evidenced in the examples below, the first variant of the invention comprising the SEQ ID NO: 1 and the amino acid substitution I153T (i.e., the variant of the invention that comprises or consists of the SEQ ID NO: 2) shows improved or enhanced selectivity for epoxidation.

Thus, another aspect of the invention refers to the use of the first variant of the invention comprising the SEQ ID NO: 1 and the amino acid substitution I153T (i.e. the variant of the invention which comprises, preferably consists of, the SEQ ID NO: 2) for the epoxidation of unsaturated fatty acids, preferably for the production of mono- and di-epoxides. The I153T mutation increases the rMroUPO selectivity towards mono- and poly-unsaturated fatty acid epoxidation, strongly reducing the ratio between simple epoxides and their hydroxylated derivatives, with respect to the rMroUPO. Thus, in another preferred embodiment of this aspect of the invention, the unsaturated fatty acids are polyunsaturated (18-carbon) fatty acids. Preferred monounsaturated fatty acids are oleic acid, and preferred polyunsaturated fatty acids are linoleic acid and/or alpha-linolenic acid.

As previously mentioned, and as evidenced in the examples below, the second variant of the invention comprising the SEQ ID NO: 1 and the amino acid substitutions I153F and S156F (i.e., the variant of the invention that comprises or consists of the SEQ ID NO: 3) shows total selectivity for hydroxylation.

Thus, another aspect of the invention refers to the use of the second variant of the invention comprising the SEQ ID NO: 1 and the amino acid substitutions I153F and S156F (i.e. the variant of the invention which comprises, preferably consists of, the SEQ ID NO: 3) for the terminal and sub-terminal hydroxylation of unsaturated fatty acids, preferably oleic acid. More preferably, this use refers to the production of ω-1 and ω hydroxy-, keto- and carboxyl-derivatives from oleic acid.

Preferably, "unsaturated fatty acids" are selected from the list consisting of: oleic acid (cis-9-octadecenoic acid), linoleic acid (cis,cis-9,12-octadecadienoic acid), alpha-linolenic acid (cis,cis,cis-9,12,15-octadecatrienoic acid) or any combination thereof.

Another aspect of the invention refers to a method for the epoxidation of unsaturated fatty acids, preferably polyunsaturated (18-carbon) fatty acids, more preferably for the production of mono- and di-epoxides, which comprises: (a) incubating, under appropriate conditions, a starting material comprising unsaturated fatty acids, preferably oleic acid, linoleic acid, alpha-linolenic acid or any combination thereof, with the first variant of the invention comprising the SEQ ID NO: 1 and the amino acid substitution I153T (i.e. the variant of the invention which comprises, preferably consists of, the SEQ ID NO: 2), and (b) recovering the epoxidation products obtained after the incubation step (a).

Another aspect of the invention refers to a method for the terminal and sub-terminal hydroxylation of unsaturated fatty acids, preferably oleic acid, more preferably for the production of ω-1 and ω hydroxy-, keto- and carboxyl-derivatives, which comprises: (a) incubating, under appropriate conditions, a starting material comprising unsaturated fatty acids, preferably oleic acid, with the second variant of the invention comprising the SEQ ID NO: 1 and the amino acid substitutions I153F and S156F (i.e. the variant of the invention which comprises, preferably consists of, the SEQ ID NO: 3) and (b) recovering the hydroxylation products obtained after the incubation step (a).

In the context of the present invention, "appropriate conditions" are, preferably, the presence of $H_2O_2$ and phosphate, a temperature of 30° C., and pH 5.5.

These methods described above may be performed at laboratory scale or at industrial scale in an industrial bioreactor.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

Example 1: Recombinant MroUPO Enzyme (rMroUPO) and its Mutated Variants

To investigate substrate epoxidation, the most frequent positions of oleic acid at the MroUPO heme-access channel were predicted by inspection of the crystal structure (Protein Data Bank entries 5FUJ and 5FUK). Then, mutations in neighbor residues were designed aiming at modulating the enzyme epoxidation vs hydroxylation ratio. Both a recombinant MroUPO (rMroUPO) and mutated variants thereof were expressed in *Escherichia coli* as active enzymes, and their action on oleic and other fatty acids was investigated by gas chromatography-mass spectrometry.

Figure 8:
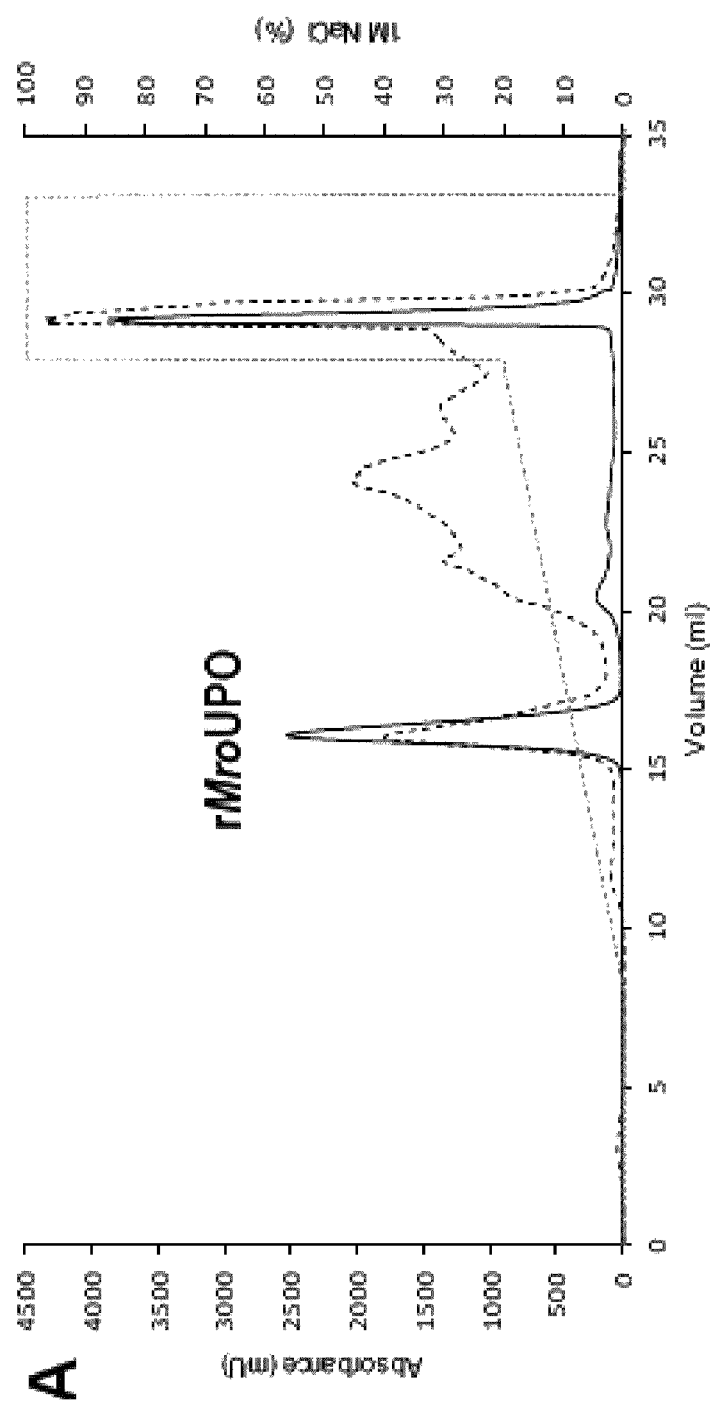
FIG. 8. Purification of rMroUPO heterologously expressed in E. coli as soluble active enzyme. (A) Mono-S chromatography showing 280 nm (dashed line) and 410 nm (continuous line) absorbance profiles and NaCl gradient (dotted line). (B) Sodium dodecylsulfate-polyacrylamide gel electrophoresis of purified rMroUPO (lane b) compared with molecular-mass standards (lane a).
Figure 8:
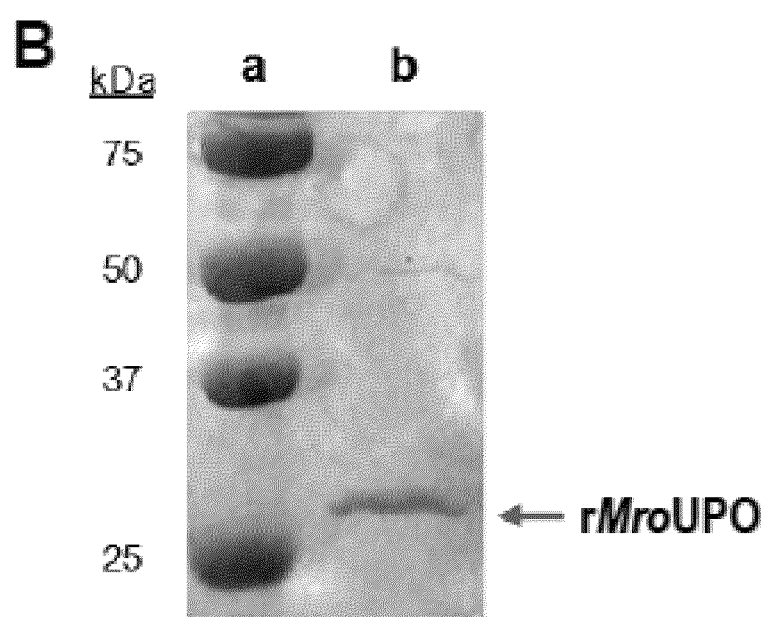

A recombinant MroUPO (rMroUPO) and its amino acid substitution I153S, I153T, I153V and I153F/S156F mutants were expressed as soluble recombinant proteins in *E. coli*. In short, cells were lysed by addition of lysozyme and sonication, and debris was removed from the soluble fraction by ultracentrifugation. Three chromatographic steps—two anionic at pH 7.0 and one final cationic at pH 4.0—were used to obtain pure enzymes. The last purification step yielded electrophoretically homogeneous enzyme (as illustrated for rMroUPO in FIG. 8).

The rMroUPO substitution mutants were prepared using the Expand Long Template PCR kit from Roche (Basel, Switzerland) for site-directed mutagenesis. PCR reactions were run using the following DNA oligos harboring the desired mismatches (underlined nucleotides in bold triplets): i) I153S mutation: 5'-CCGATTTAACTGCGACT TC CCGCTCTTCAGAATCTG-3' (SEQ ID NO: 5); ii) I153T mutation: 5'-CCGATTTAACTGCGACTA C CCGCTCTTCAGAATCTG-3' (SEQ ID NO: 6); iii) I153V mutation: 5'-CCGATTTAACTGCGACT G TCCGCTCTTCAGAATCTG-3' (SEQ ID NO: 7); and iv) I153F/S156F mutation: 5'-CCGATTTAACTGCGACT T TCCGCTCTT TC GAATCTGCG-3' (SEQ ID NO: 8), along with their reverse complementary counterparts.

The PCR reactions (50 µl volume) were carried out in an Eppendorf (Hamburg, Germany) Mastercycler pro-S using 30 ng of template DNA, 500 µM each dNTP, 125 ng forward and reverse primers, 5 units of Expand Long Template PCR System polymerase mix (Roche), and the manufacturer buffer. Reaction conditions included: i) initial denaturation step of 1 min at 95° C.; ii) 22 cycles of 30 s at 95° C., 30 s at 60° C., and 7 min at 68° C., each; and iii) final elongation step of 7 min at 68° C. The mutated upo genes were expressed in *E. coli* as described above.

Example 2: Oleic Acid Reactions with rMroUPO Mutated Variants

Simple (I153S, I153T and I153V) and double (I153F/S156F) mutations-which could potentially improve or abolish, respectively, the epoxidation ability of MroUPO-were experimentally introduced by site-directed mutagenesis and the mutated genes were transformed into *E. coli* as explained in Example 1. However, only I153T and I153F/S156F could be obtained as soluble active enzymes.

Interestingly, a small modification of the channel shape in the I153T variant increased the ratio between stearic acid epoxide and its additionally hydroxylated derivatives. A fully opposite effect was attained with the double I153F/S156F variant that completely abolished the MroUPO ability to epoxidize oleic acid.

Example 3: Reaction of the rMroUPO with Oleic Acid (Cis-9-Octadecenoic Acid)

rMroUPO (SEQ ID NO: 1) was expressed using the protocol described in Example 1, after transformation of the pET23b plasmid harbouring the mroupo gene into *Escherichia coli* BL21 C41 cells. The said enzyme was obtained as a soluble active protein, and purified to electrophoretic homogeneity through several ion-exchange chromatographic steps.

The rMroUPO (0.2 µM) was incubated with oleic acid (100 µM) and $H_2O_2$ (2,500 µM) at 30° C. in 50 mM phosphate, pH 5.5, for 30 min. Oleic acid had been previously dissolved in acetone so that the final acetone concentration attained 20% (v/v) in the embodiment. After the incubation time, the products were recovered by liquid-liquid extraction with t-butyl-methyl-ether. The organic solvent was removed under $N_2$ current. N,O-Bis-(trimethylsilyl)trifluoroacetamide was employed to prepare the trimethylsilyl derivatives of the compounds to be separated by gas chromatography and identified by mass spectrometry.

Chromatographic analyses were carried out in a gas chromatograph coupled to a mass-spectrometry detector. The column used was a fused-silica DB-5HT capillary column (30 m×0.25 mm internal diameter×0.1 µm film thickness). Oven was heated from 120° C. (1 min) to 300° C. (5 min) at 5° C.·min. Injection was performed at 300° C. and transfer line was maintained at 300° C. Compounds were identified by comparison of their mass spectra with those of authentic standards and those from the NIST and Wiley libraries as well as by mass fragmentography. Quantification of the products was carried out by integrating the total ion peak areas, using external standard curves of the same or closely related compounds.

Figure 1:
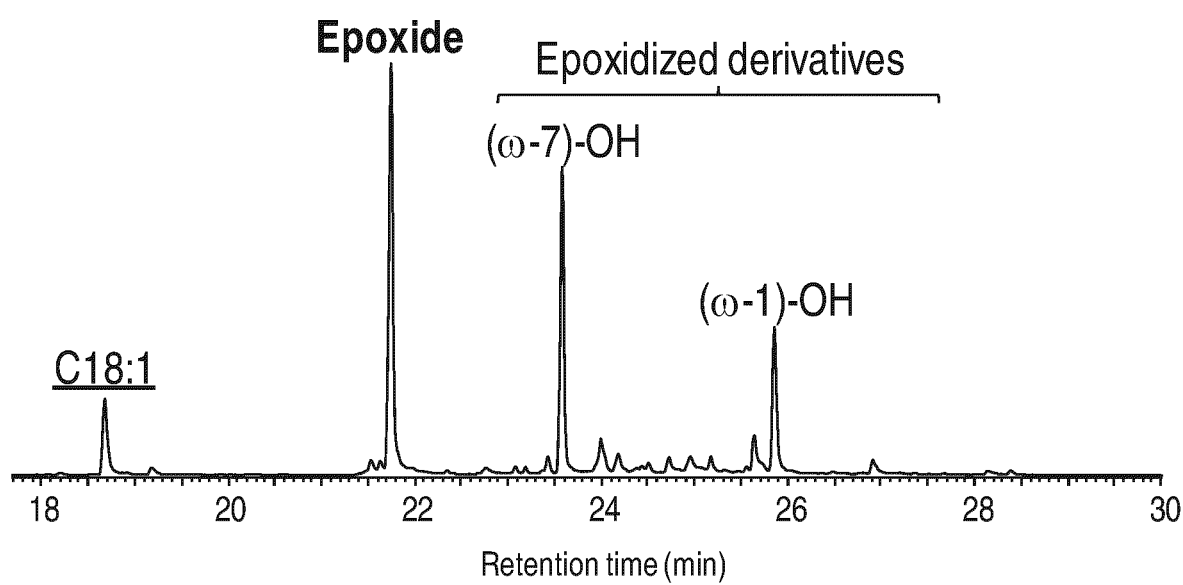
FIG. 1. Chromatogram that shows the products (and remaining substrate, underlined) of the reaction of rMroUPO (0.2 μM) with oleic acid (cis-9-octadecenoic acid; 0.1 μM) and $H_2O_2$ (2,500 μM), performed in 50 mM phosphate, pH 5.5, at 30° C. for 30 min, analyzed by gas chromatography-mass spectrometry.

A chromatogram of the products obtained in the embodiment is illustrated in FIG. 1. rMroUPO produces the epoxide between $C_9$-$C_{10}$, as well as the ($\omega$-7) and ($\omega$-1) hydroxylated derivatives of the said epoxide, labelled as ($\omega$-7)-OH and ($\omega$-1)-OH, respectively. Conversion of the substrate (oleic acid) into substrates attained 94%, being 40% of the products only epoxides and 57% other (hydroxylated) epoxides. Therefore, the selectivity towards only epoxidation is of 0.67 (estimated as the ratio between only epoxides and other oxygenation products).

Example 4: Reaction of the rMroUPO I153T Mutated Variant with Oleic Acid (Cis-9-Octadecenoic Acid)

The rMroUPO I153T mutated variant (SEQ ID NO: 2), in which isoleucine 153 was replaced by threonine, was constructed by site-directed mutagenesis, in a PCR reaction in which the following oligos—complementary to the regions of the gene to be mutated, but bearing the desired mismatches—were used as primers: 5'-CCGATT-TAACTGCGACTACCCGCTCTTCAGAATCTG-3' (SEQ ID NO: 6), along with its reverse complementary counterpart. The PCR reactions were performed in a thermocycler, adding 30 ng of template DNA—plasmid pET23b with the mroupo gene as an insert—, 500 µM each dNTP, 125 ng primers, 5 units of polymerase mix, and buffer to a final volume of 50 µl. Reaction conditions were as follows: i) initial denaturation step of 1 min at 95° C.; ii) 22 cycles of 30 s at 95° C., 30 s at 60° C., and 7 min at 68° C., each; and iii) final elongation step of 7 min at 68° C. PCR products were treated with restriction enzyme DpnI at 37° C. for 1 h in order to degrade parental (non-mutated) DNA.

The mutated DNA was transformed into *Escherichia coli* DH5a cells to propagate the DNA obtained. Mutation was confirmed by sequencing the gene encoding the protein using the T7 promoter primers.

Expression and purification of the enzyme was carried out as described in Example 3 for rMroUPO.

Reactions with oleic acid and identification and quantification of the products were conducted as explained in Example 3.

Figure 2:
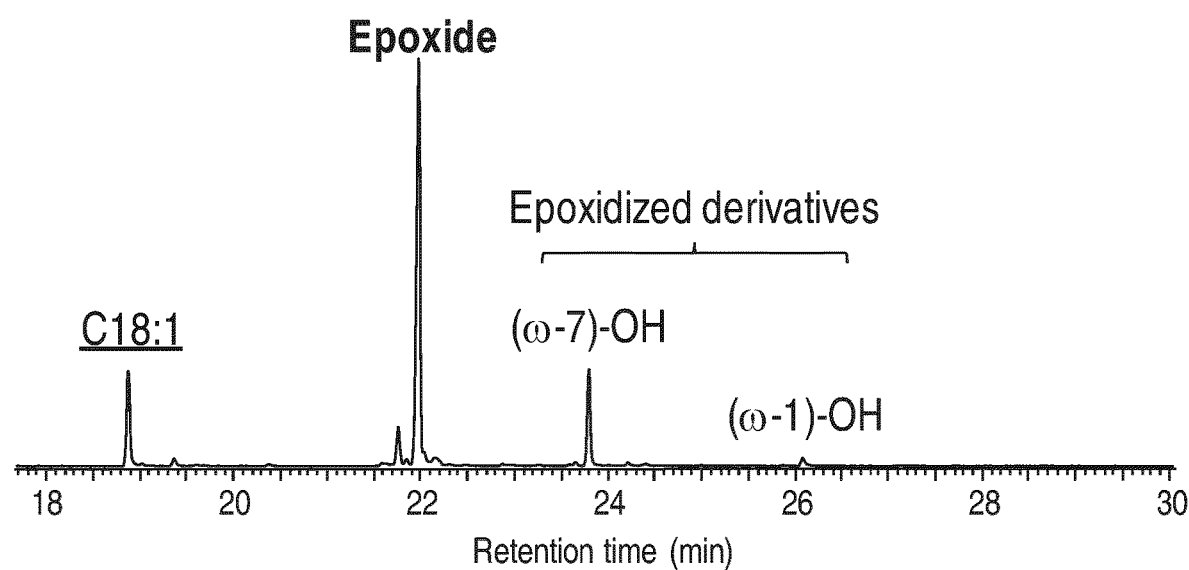
FIG. 2. Chromatogram that shows the products (and remaining substrate, underlined) of the reaction of rMroUPO I153T mutated variant (0.2 μM) with oleic acid (cis-9-octadecenoic acid; 0.1 μM) and $H_2O_2$ (2,500 μM), performed in 50 mM phosphate, pH 5.5, at 30° C. for 30 min, analyzed by gas chromatography-mass spectrometry.

As depicted in FIG. 2, reaction of the rMroUPO I153T mutated variant with oleic acid gave rise to the same products than rMroUPO, although with very different relative abundances. Conversion into products reached 85%, constituting only epoxides the 72% and other (hydroxylated) epoxide derivatives 17%. Therefore, the selectivity towards only epoxidation (defined in Example 3) attained a 2.67 value.

Example 5: Reaction of the rMroUPO I153F/S156F Mutated Variant with Oleic Acid (Cis-9-Octadecenoic Acid)

The rMroUPO I153F/S156F mutated variant (SEQ ID NO: 3), in which isoleucine 153 and serine 156 were both replaced by phenylalanine residues, was constructed by site-directed mutagenesis, in a PCR reaction in which the following oligos—complementary to the region of the gene to be mutated, but bearing the desired mismatches—were used as primers: 5'-CCGATT-TAACTGCGACTTTCCGCTCTTTCGAATCTGCG-3' (SEQ ID NO: 8), along with its reverse complementary counterpart. PCR reaction and sequencing of the mutated variant were carried out as described in Example 4. Expression, purification of the enzyme, reactions with oleic acid and GC-MS identification and quantification of the products were conducted as in Example 3.

Figure 3:
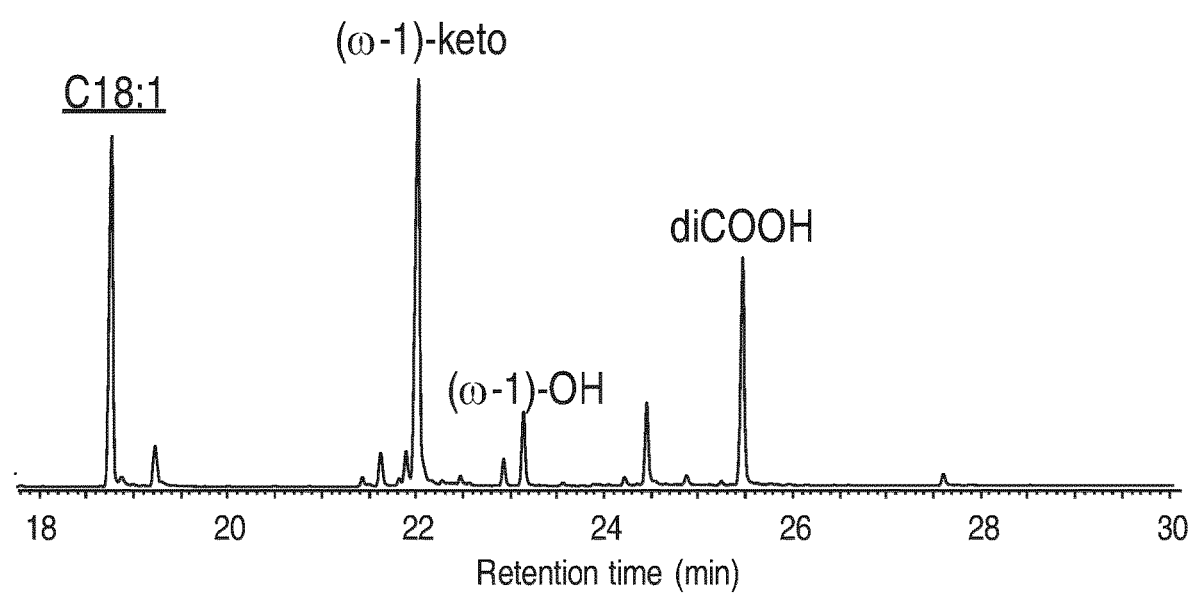
FIG. 3. Chromatogram that shows the products (and remaining substrate, underlined) of the reaction of rMroUPO I153F/S156F mutated variant (0.2 μM) with oleic acid (cis-9-octadecenoic acid; 0.1 μM) and $H_2O_2$ (2,500 μM), performed in 50 mM phosphate, pH 5.5, at 30° C. for 30 min, analyzed by gas chromatography-mass spectrometry.

FIG. 3 depicts a chromatogram of the products obtained, which were restricted to ω-1 and ω hydroxylated, keto and carboxylic species derived from oleic acid, all resulting from the hydroxylation (and re-hydroxylation) of the oleic acid. No traces of epoxidized species were detected. Therefore, the selectivity of this MroUPO I153F/S156F mutated variant is total towards hydroxylation.

Example 6: Reaction of the rMroUPO with Linoleic Acid (Cis,Cis-9,12-Octadecadienoic Acid)

Expression and purification of rMroUPO (SEQ ID NO: 1) were carried out as described in Example 3.

An embodiment was designed in which rMroUPO (0.6 µM) was incubated with linoleic acid (100 µM, previously dissolved in acetone so that the final acetone concentration in the embodiment was of 20%) and $H_2O_2$ (1,250 µM) at 30° C. in 50 mM phosphate, pH 5.5, for 30 min. Identification and quantification of the products was conducted as detailed in Example 3.

Figure 4:
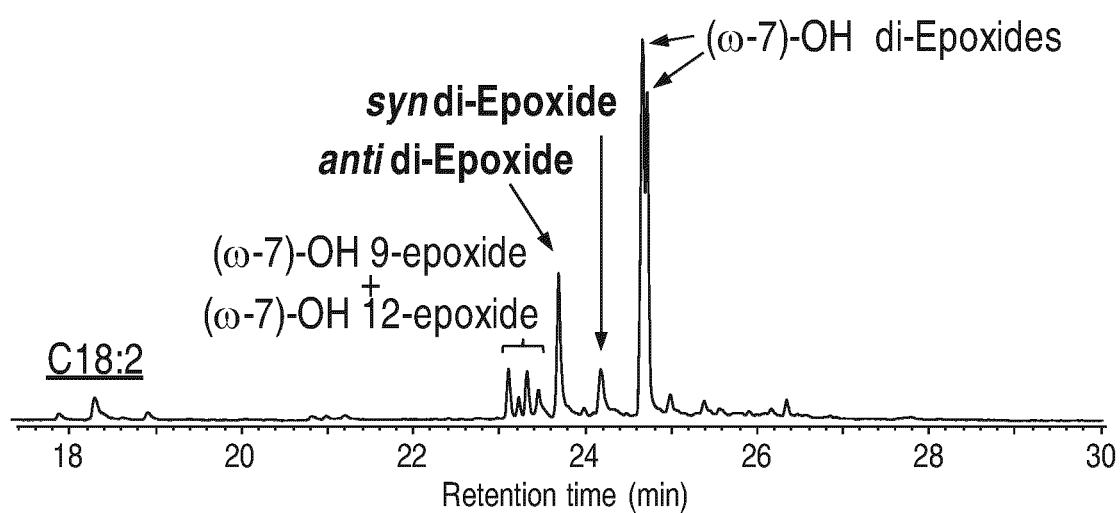
FIG. 4. Chromatogram that shows the products (and remaining substrate, underlined) of the reaction of rMroUPO (0.6 μM) with linoleic acid (cis,cis-9,12-octadecadienoic acid; 0.1 μM) and $H_2O_2$ (1,250 μM), performed in 50 mM phosphate, pH 5.5, at 30° C. for 30 min, analyzed by gas chromatography-mass spectrometry.

FIG. 4 illustrates the chromatogram of the products of the said embodiment. The main products were di-epoxides (anti and syn isomers) and hydroxylated mono- and di-epoxides. Conversion attained 98%, of which 21% were only epoxides, and 79% hydroxylated epoxides. Thus, the selectivity towards only epoxidation was of 0.27.

Example 7: Reaction of the rMroUPO I153T Mutated Variant with Linoleic Acid (Cis,Cis-9,12-Octadecadienoic Acid)

Construction of the rMroUPO I153T mutated variant (SEQ ID NO: 2) was carried out as described in Example 4. Expression and purification of the mutant was as detailed in Example 3.

Reactions were performed as in Example 6. Identification and quantification of the products is described in Example 3.

Figure 5:
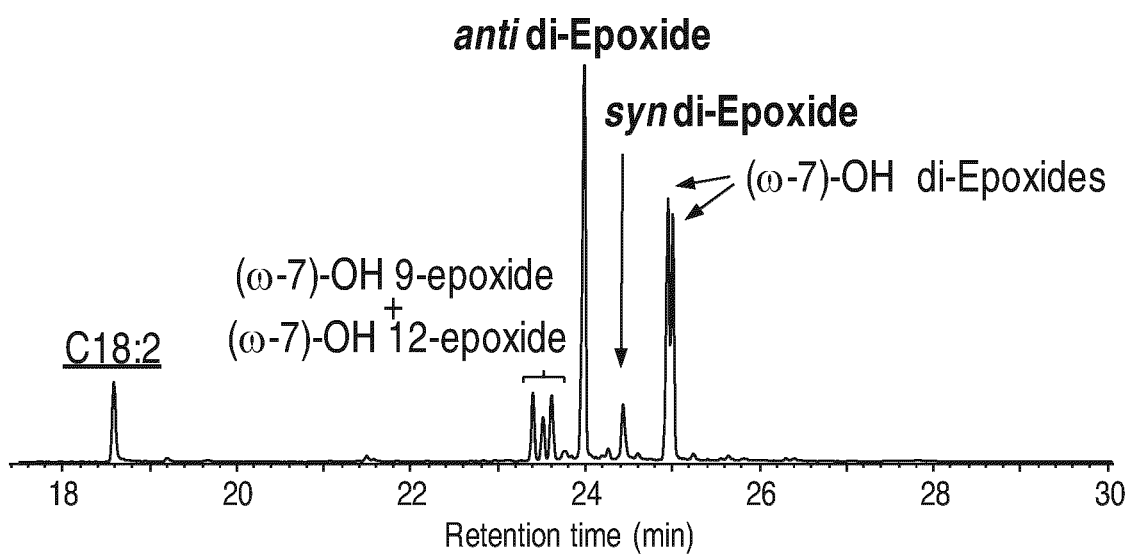
FIG. 5. Chromatogram that shows the products (and remaining substrate, underlined) of the reaction of rMroUPO I153T mutated variant (0.6 μM) with linoleic acid (cis,cis-9,12-octadecadienoic acid; 0.1 μM) and $H_2O_2$ (1,250 μM), performed in 50 mM phosphate, pH 5.5, at 30° C. for 30 min, analyzed by gas chromatography-mass spectrometry.

FIG. 5 depicts a chromatogram of the products obtained in the embodiment. The main products were di-epoxides (anti and syn isomers) and hydroxylated mono- and di-epoxides. Conversion attained 93%, of which 42% were only epoxides, and 58% hydroxylated epoxides. Thus, the selectivity towards only epoxidation was of 0.72, which represents an improvement in the epoxidation selectivity of this variant compared to the rMroUPO (SEQ ID NO: 1).

Example 8: Reaction of the rMroUPO with α-Linolenic Acid (Cis,Cis,Cis-9,12,15-Octadecatrienoic Acid)

Expression and purification of rMroUPO (SEQ ID NO: 1) was carried out as described in Example 3.

Reactions were performed in an embodiment consisting of rMroUPO (0.2 µM), incubated with α-linolenic acid (100 µM) and $H_2O_2$ (1,250 µM) at 30° C., in 50 mM phosphate, pH 5.5, for 30 min. Extraction and separation of the reaction products was carried out as described in Example 3. Since no available commercial standards of epoxidized α-linolenic acid were available, they were chemically synthesised as follows: a solution of peracetic acid (1.8 mmol, 3.6 equiv) and NaOAc (0.7 mmol; 1.4 equiv) was added to α-linolenic acid (0.5 mmol) using a syringe pump at 0° C. for 1 h. The mixture was stirred at 0° C. for an additional h. Products were recovered by liquid-liquid extraction with t-butyl-methyl-ether, resulting in a mixture of mono- and di-epoxides. Identification of the compounds was made by comparison of the mass spectra with those of the synthesised standards and by mass fragmentography. Quantification was carried out as detailed in Example 3.

Figure 6:
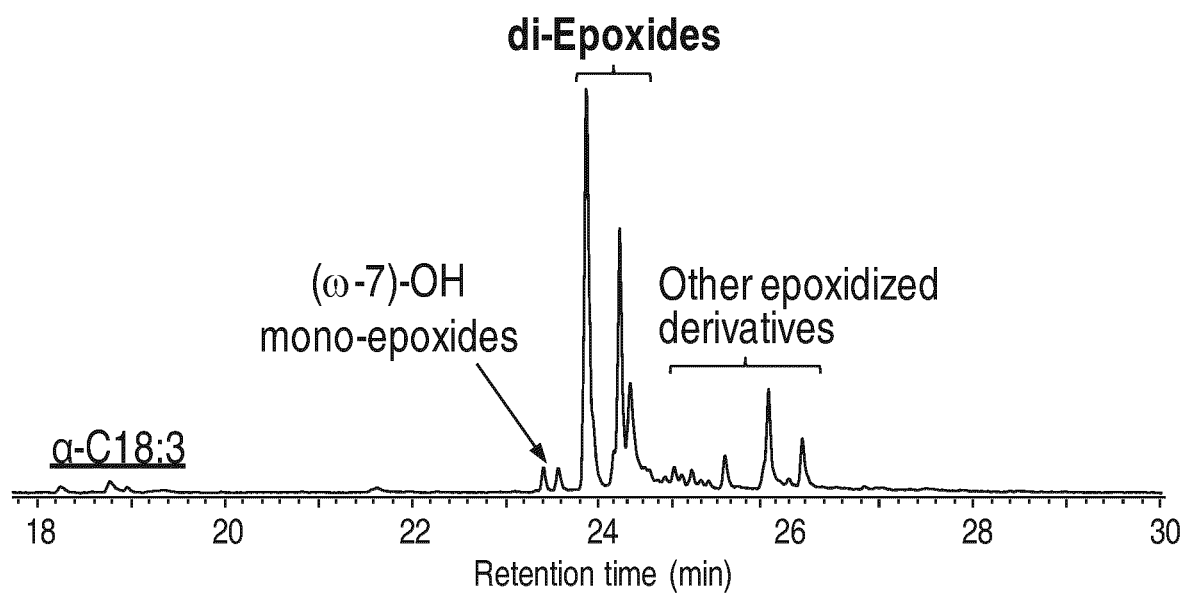
FIG. 6. Chromatogram that shows the products (and remaining substrate, underlined) of the reaction of rMroUPO (0.2 μM) with α-linolenic acid (cis,cis,cis-9,12,15-octadecatrienoic acid; 0.1 μM) and $H_2O_2$ (1,250 μM), performed in 50 mM phosphate, pH 5.5, at 30° C. for 30 min, analyzed by gas chromatography-mass spectrometry.

FIG. 6 illustrates a chromatogram of the products obtained in the reaction. The main products included: di-epoxides, other epoxidized derivatives and (ω-7)-OH monoepoxides. Conversion reached 98%, of which only epoxides were 44%, while other epoxides represented the 56%. Therefore, the selectivity towards only epoxidation was of 0.79.

Example 9: Reaction of the rMroUPO I153T Mutated Variant with α-Linolenic Acid (Cis,Cis,Cis-9,12,15-Octadecatrienoic Acid)

Construction of the rMroUPO I153T mutated variant (SEQ ID NO: 2), expression and purification of the mutant was carried out as described in Example 4.

Figure 7:
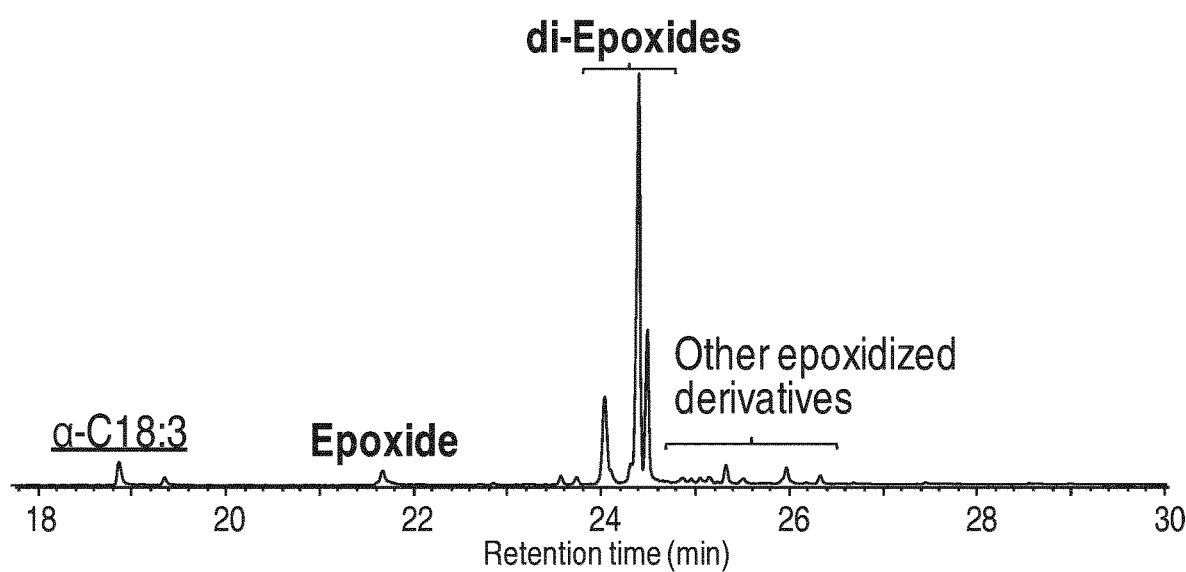
FIG. 7. Chromatogram that shows the products (and remaining substrate, underlined) of the reaction of rMroUPO I153T mutated variant (0.2 μM) with α-linolenic acid (cis,cis,cis-9,12,15-octadecatrienoic acid; 0.1 μM) and $H_2O_2$ (1,250 μM), performed in 50 mM phosphate, pH 5.5, at 30° C. for 30 min, analyzed by gas chromatography-mass spectrometry.

Reactions and analyses of the products were performed as in Example 8. FIG. 7 illustrates a chromatogram of the reaction products, among which single epoxides, di-epoxides and other epoxidized derivatives. Conversion of the substrate attained 97%, of which 92% (of which 88% are di-epoxides) represented only epoxides and a mere 8% other epoxide derivatives. Therefore, the selectivity towards only epoxidation reached 11.50.

The invention claimed is:

1. A recombinant peroxygenase enzyme that comprises the amino acid sequence shown in SEQ ID NO: 2, wherein said enzyme is encoded by a polynucleotide sequence with at least 90%, 91%, 92%, 93%, 94%, 95%, 96%, 97%, 98% or 99% sequence identity with SEQ ID NO: 9.

2. A method for the epoxidation of unsaturated fatty acids which comprises the steps:
(a) Incubating a starting material comprising unsaturated fatty acids with the recombinant peroxygenase according to claim 1;
(b) Recovering the epoxidation products obtained after the incubation step (a).

3. The method according to claim 2, wherein the unsaturated fatty acids are polyunsaturated fatty acids.

4. The method according to claim 3, wherein the unsaturated fatty acids are selected from the list consisting of: oleic acid, linoleic acid, alpha-linolenic acid or any combination thereof.

* * * * *

SEQUENCE LISTING

<160> NUMBER OF SEQ ID NOS: 9

<210> SEQ ID NO 1

<211> LENGTH: 236
<212> TYPE: PRT
<213> ORGANISM: Artificial Sequence
<220> FEATURE:
<223> OTHER INFORMATION: Recombinant Marasmius rotula unspecific
      peroxygenase enzyme, rMroUPO

<400> SEQUENCE: 1

```
Ser Ala His Pro Trp Lys Ala Pro Gly Pro Asn Asp Ser Arg Gly Pro
1               5                   10                  15

Cys Pro Gly Leu Asn Thr Leu Ala Asn His Gly Phe Leu Pro Arg Asn
            20                  25                  30

Gly Arg Asn Ile Ser Val Pro Met Ile Val Lys Ala Gly Phe Glu Gly
        35                  40                  45

Tyr Asn Val Gln Ser Asp Ile Leu Ile Leu Ala Gly Lys Ile Gly Met
    50                  55                  60

Leu Thr Ser Arg Glu Ala Asp Thr Ile Ser Leu Glu Asp Leu Lys Leu
65                  70                  75                  80

His Gly Thr Ile Glu His Asp Ala Ser Leu Ser Arg Glu Asp Val Ala
                85                  90                  95

Ile Gly Asp Asn Leu His Phe Asn Glu Ala Ile Phe Thr Thr Leu Ala
            100                 105                 110

Asn Ser Asn Pro Gly Ala Asp Val Tyr Asn Ile Ser Ser Ala Ala Gln
        115                 120                 125

Val Gln His Asp Arg Leu Ala Asp Ser Leu Ala Arg Asn Pro Asn Val
    130                 135                 140

Thr Asn Thr Asp Leu Thr Ala Thr Ile Arg Ser Ser Glu Ser Ala Phe
145                 150                 155                 160

Phe Leu Thr Val Met Ser Ala Gly Asp Pro Leu Arg Gly Glu Ala Pro
                165                 170                 175

Lys Lys Phe Val Asn Val Phe Phe Arg Glu Glu Arg Met Pro Ile Lys
            180                 185                 190

Glu Gly Trp Lys Arg Ser Thr Thr Pro Ile Thr Ile Pro Leu Leu Gly
        195                 200                 205

Pro Ile Ile Glu Arg Ile Thr Glu Leu Ser Asp Trp Lys Pro Thr Gly
    210                 215                 220

Asp Asn Cys Gly Ala Ile Val Leu Ser Pro Glu Leu
225                 230                 235
```

<210> SEQ ID NO 2
<211> LENGTH: 236
<212> TYPE: PRT
<213> ORGANISM: Artificial Sequence
<220> FEATURE:
<223> OTHER INFORMATION: Variant of the invention which comprises the
      SEQ ID NO: 1 and the amino acid substitution I153T

<400> SEQUENCE: 2

```
Ser Ala His Pro Trp Lys Ala Pro Gly Pro Asn Asp Ser Arg Gly Pro
1               5                   10                  15

Cys Pro Gly Leu Asn Thr Leu Ala Asn His Gly Phe Leu Pro Arg Asn
            20                  25                  30

Gly Arg Asn Ile Ser Val Pro Met Ile Val Lys Ala Gly Phe Glu Gly
        35                  40                  45

Tyr Asn Val Gln Ser Asp Ile Leu Ile Leu Ala Gly Lys Ile Gly Met
    50                  55                  60

Leu Thr Ser Arg Glu Ala Asp Thr Ile Ser Leu Glu Asp Leu Lys Leu
65                  70                  75                  80
```

His Gly Thr Ile Glu His Asp Ala Ser Leu Ser Arg Glu Asp Val Ala
                85                  90                  95

Ile Gly Asp Asn Leu His Phe Asn Glu Ala Ile Phe Thr Thr Leu Ala
            100                 105                 110

Asn Ser Asn Pro Gly Ala Asp Val Tyr Asn Ile Ser Ser Ala Ala Gln
        115                 120                 125

Val Gln His Asp Arg Leu Ala Asp Ser Leu Ala Arg Asn Pro Asn Val
    130                 135                 140

Thr Asn Thr Asp Leu Thr Ala Thr Thr Arg Ser Ser Glu Ser Ala Phe
145                 150                 155                 160

Phe Leu Thr Val Met Ser Ala Gly Asp Pro Leu Arg Gly Glu Ala Pro
                165                 170                 175

Lys Lys Phe Val Asn Val Phe Phe Arg Glu Glu Arg Met Pro Ile Lys
            180                 185                 190

Glu Gly Trp Lys Arg Ser Thr Thr Pro Ile Thr Ile Pro Leu Leu Gly
        195                 200                 205

Pro Ile Ile Glu Arg Ile Thr Glu Leu Ser Asp Trp Lys Pro Thr Gly
    210                 215                 220

Asp Asn Cys Gly Ala Ile Val Leu Ser Pro Glu Leu
225                 230                 235

<210> SEQ ID NO 3
<211> LENGTH: 236
<212> TYPE: PRT
<213> ORGANISM: Artificial Sequence
<220> FEATURE:
<223> OTHER INFORMATION: Variant of the invention which comprises the
      SEQ ID NO: 1 and the amino acid substitutions I153F and S156F

<400> SEQUENCE: 3

Ser Ala His Pro Trp Lys Ala Pro Gly Pro Asn Asp Ser Arg Gly Pro
1               5                   10                  15

Cys Pro Gly Leu Asn Thr Leu Ala Asn His Gly Phe Leu Pro Arg Asn
            20                  25                  30

Gly Arg Asn Ile Ser Val Pro Met Ile Val Lys Ala Gly Phe Glu Gly
        35                  40                  45

Tyr Asn Val Gln Ser Asp Ile Leu Ile Leu Ala Gly Lys Ile Gly Met
    50                  55                  60

Leu Thr Ser Arg Glu Ala Asp Thr Ile Ser Leu Glu Asp Leu Lys Leu
65                  70                  75                  80

His Gly Thr Ile Glu His Asp Ala Ser Leu Ser Arg Glu Asp Val Ala
                85                  90                  95

Ile Gly Asp Asn Leu His Phe Asn Glu Ala Ile Phe Thr Thr Leu Ala
            100                 105                 110

Asn Ser Asn Pro Gly Ala Asp Val Tyr Asn Ile Ser Ser Ala Ala Gln
        115                 120                 125

Val Gln His Asp Arg Leu Ala Asp Ser Leu Ala Arg Asn Pro Asn Val
    130                 135                 140

Thr Asn Thr Asp Leu Thr Ala Thr Phe Arg Ser Phe Glu Ser Ala Phe
145                 150                 155                 160

Phe Leu Thr Val Met Ser Ala Gly Asp Pro Leu Arg Gly Glu Ala Pro
                165                 170                 175

Lys Lys Phe Val Asn Val Phe Phe Arg Glu Glu Arg Met Pro Ile Lys
            180                 185                 190

Glu Gly Trp Lys Arg Ser Thr Thr Pro Ile Thr Ile Pro Leu Leu Gly

```
                195                 200                 205
Pro Ile Ile Glu Arg Ile Thr Glu Leu Ser Asp Trp Lys Pro Thr Gly
    210                 215                 220

Asp Asn Cys Gly Ala Ile Val Leu Ser Pro Glu Leu
225                 230                 235
```

<210> SEQ ID NO 4
<211> LENGTH: 28
<212> TYPE: PRT
<213> ORGANISM: Artificial Sequence
<220> FEATURE:
<223> OTHER INFORMATION: Signal peptide

<400> SEQUENCE: 4

```
Met Lys Leu Ala Ile Ser Ser Ser Leu Ile Ala Leu Val Ser Val Thr
1               5                   10                  15

Thr Ala Leu Ala Asn Ser Gln Asp Val Val Asp Phe
            20                  25
```

<210> SEQ ID NO 5
<211> LENGTH: 36
<212> TYPE: DNA
<213> ORGANISM: Artificial Sequence
<220> FEATURE:
<223> OTHER INFORMATION: Forward primer for the I153S mutation

<400> SEQUENCE: 5
ccgatttaac tgcgacttcc cgctcttcag aatctg                               36

<210> SEQ ID NO 6
<211> LENGTH: 36
<212> TYPE: DNA
<213> ORGANISM: Artificial Sequence
<220> FEATURE:
<223> OTHER INFORMATION: Forward primer for the I153T mutation

<400> SEQUENCE: 6
ccgatttaac tgcgactacc cgctcttcag aatctg                               36

<210> SEQ ID NO 7
<211> LENGTH: 36
<212> TYPE: DNA
<213> ORGANISM: Artificial Sequence
<220> FEATURE:
<223> OTHER INFORMATION: Forward primer for the I153V mutation

<400> SEQUENCE: 7
ccgatttaac tgcgactgtc cgctcttcag aatctg                               36

<210> SEQ ID NO 8
<211> LENGTH: 38
<212> TYPE: DNA
<213> ORGANISM: Artificial Sequence
<220> FEATURE:
<223> OTHER INFORMATION: Forward primer for the I153F/S156F mutation

<400> SEQUENCE: 8
ccgatttaac tgcgactttc cgctctttcg aatctgcg                             38

<210> SEQ ID NO 9
<211> LENGTH: 795
<212> TYPE: DNA
<213> ORGANISM: Artificial Sequence
<220> FEATURE:
<223> OTHER INFORMATION: Polynucleotide sequence that encodes the enzyme shown in SEQ ID NO: 1

<400> SEQUENCE: 9

```
atgaaactgg cgatctcttc cagcctgatc gccctcgtct cggttaccac agctctggct     60
aacagccaag acgtagttga cttctccgca catccgtgga aagctccggg tccgaacgac    120
tctcgcggtc cgtgcccagg cctgaacact ctggctaacc acggcttcct gccgcgtaat    180
ggtcgtaaca tctccgtacc gatgattgtg aaagccggct tcgagggtta caacgtccag    240
agcgacatcc tgatcctcgc cggtaaaatc ggtatgctga cgtcgcgtga agctgatacc    300
atatcgttgg aagatctgaa actgcacggt accatcgaac acgatgcatc tctgagccgc    360
gaggatgtag cgattggtga taacctgcac ttcaacgagg caattttcac caccctggct    420
aactccaacc ctggtgcaga cgtttataac atttctagcg cggctcaggt gcagcatgat    480
cgtctggcag actctctggc gcgcaacccg aacgttacta acaccgattt aactgcgact    540
atccgctctt cagaatctgc gttcttcctg accgttatgt ccgcaggcga tccgctgcgt    600
ggtgaagcgc cgaagaaatt cgtgaacgtc ttctttcgtg aagaacgcat gccgattaaa    660
gaaggttgga aacgttccac caccccgatc actattccgc ttctgggtcc gatcattgag    720
cgcatcacgg aattatcgga ctggaaacca actggcgata actgcggcgc tatcgttctc    780
agcccggaac tgtaa                                                     795
```